(12) United States Patent
Feng

(10) Patent No.: US 8,906,350 B2
(45) Date of Patent: Dec. 9, 2014

(54) TOOTH WHITENING ACCELERATOR FORMULATION AND METHOD OF USING THE SAME

(75) Inventor: Jianxun Feng, Santa Maria, CA (US)

(73) Assignee: Gosmile, Inc., Berkeley, CA (US)

( * ) Notice: Subject to any disclaimer, the term of this patent is extended or adjusted under 35 U.S.C. 154(b) by 98 days.

(21) Appl. No.: 13/010,526

(22) Filed: Jan. 20, 2011

(65) Prior Publication Data

US 2011/0177013 A1    Jul. 21, 2011

Related U.S. Application Data

(60) Provisional application No. 61/296,789, filed on Jan. 20, 2010.

(51) Int. Cl.
| | | |
|---|---|---|
| *A61K 8/58* | (2006.01) | |
| *A61Q 11/02* | (2006.01) | |
| *A61K 8/34* | (2006.01) | |
| *A61Q 11/00* | (2006.01) | |
| *A61K 8/49* | (2006.01) | |
| *A61K 8/19* | (2006.01) | |
| *A61K 8/86* | (2006.01) | |
| *A61K 8/39* | (2006.01) | |
| *A61K 8/81* | (2006.01) | |

(52) U.S. Cl.
CPC ............... *A61Q 11/00* (2013.01); *A61K 8/345* (2013.01); *A61K 8/498* (2013.01); *A61K 8/19* (2013.01); *A61K 8/86* (2013.01); *A61K 8/39* (2013.01); *A61K 8/8129* (2013.01)
USPC .............................. 424/53; 424/49; 424/401

(58) Field of Classification Search
USPC .......................................................... 510/499
See application file for complete search history.

(56) References Cited

U.S. PATENT DOCUMENTS

| | | | | |
|---|---|---|---|---|
| 3,562,385 | A * | 2/1971 | Block et al. ..................... 424/54 |
| 4,374,824 | A * | 2/1983 | Wahmi ............................. 424/58 |
| 4,405,599 | A * | 9/1983 | Smigel ............................. 424/53 |
| 5,328,682 | A * | 7/1994 | Pullen et al. .................... 424/49 |
| 5,624,906 | A * | 4/1997 | Vermeer .......................... 514/23 |
| 7,201,577 | B2 | 4/2007 | Levine |
| 2003/0228264 | A1 | 12/2003 | Perna |
| 2006/0247150 | A1 * | 11/2006 | Molinaro et al. ............. 510/499 |
| 2008/0095811 | A1 | 4/2008 | Chen |
| 2008/0311057 | A1 * | 12/2008 | Larsen et al. .................... 424/51 |
| 2009/0214450 | A1 | 8/2009 | Fisher et al. |

FOREIGN PATENT DOCUMENTS

| | | |
|---|---|---|
| JP | 58-049309 A | 3/1983 |
| JP | 04-124112 A | 4/1992 |
| WO | WO-2005/041911 A1 | 5/2005 |

* cited by examiner

*Primary Examiner* — Walter Webb
(74) *Attorney, Agent, or Firm* — Marshall, Gerstein & Borun LLP

(57) ABSTRACT

In an embodiment, a tooth whitening accelerator composition includes a salt of boric acid dissolved in a polyol carrier. The tooth whitening accelerator composition can be used in a method of whitening teeth that includes applying the tooth whitening accelerator to teeth and applying a tooth whitening formulation to the teeth.

23 Claims, No Drawings

TOOTH WHITENING ACCELERATOR FORMULATION AND METHOD OF USING THE SAME

CROSS-REFERENCE TO RELATED APPLICATION

The benefit under 35 U.S.C. §119(e) of U.S. Provisional Patent Application No. 61/296,789, filed Jan. 20, 2010, is hereby claimed, and the disclosure is incorporated herein by reference.

BACKGROUND

1. Field of the Invention

The invention relates generally to a tooth whitening accelerator composition and method of using the same to enhance the whitening power of a whitening formulation and, more particularly, to a tooth whitening accelerator composition that includes a salt of boric acid and a polyol carrier and a method of using the same.

2. Brief Description of Related Technology

Tooth whitening has become popular with many consumers, as many desire to have a white and bright smile. Consumers desire whitening systems that offer whiter teeth in shorter amounts of time, and with less tooth sensitivity. Conventional tooth whitening formulations include a peroxide based formulation to effect whitening of the teeth. Conventional tooth whitening accelerator compositions generally function to whiten teeth by providing an abrasive element that mechanically whitens teeth, thereby enhancing the chemical whitening effect of the tooth whitening formulation. When the abrasive agent is used, there is a potential to damage the tooth surface and the tooth enamel.

SUMMARY

In one embodiment, a tooth whitening accelerator composition includes a salt of boric acid (a) dissolved in a polyol carrier, or (b) dispersed in a polyol carrier, wherein when the salt of boric acid is dispersed in the polyol carrier, the polyol carrier is included in the composition at a concentration of greater than 5% by weight of the total composition. The tooth whitening accelerator composition can optionally include an additive selected from the group consisting of a solvent, a tooth desensitizing agent, a thickening agent, a pH adjusting agent, a solvent, a flavoring agent, a tackifying agent, a preservative, and combinations thereof.

In yet another embodiment, a method of whitening teeth includes applying one of a tooth whitening accelerator composition and a tooth whitening formulation to a tooth, and applying the other one of the tooth whitening formulation and the tooth whitening accelerator composition to the tooth, over the applied tooth whitening accelerator composition or tooth whitening formulation, after the application of the one of the tooth whitening accelerator composition and the tooth whitening formulation. The tooth whitening accelerator composition includes a polyol carrier and a salt of boric acid.

In another embodiment, a method of making a tooth whitening accelerator composition includes (a) dissolving a salt of boric acid in a polyol carrier, or (b) dispersing the salt of boric acid in the polyol carrier to form a mixture, wherein when the salt of boric acid is dispersed in the polyol carrier, the polyol carrier is included in the composition at a concentration greater than 5% by weight of the total composition to form a mixture. The method can optionally include thereafter adding an additive selected from the group consisting of solvents, tooth desensitizing agents, tackifying agents, thickening agents, preservatives, flavoring agents, pH adjusting agents, and combinations thereof.

The above and other aspects and advantages will become apparent from the following detailed description.

DETAILED DESCRIPTION

Weight percents are expressed herein as the percent of the component based on the total weight of the composition.

In accordance with an embodiment of the disclosure, a tooth whitening accelerator composition includes a salt of boric acid dissolved or dispersed in a polyol carrier. The salt of boric acid can be dispersed in the polyol carrier and the polyol carrier is included in the composition at a concentration greater than about 5% by weight of the total composition. The tooth whitening accelerator composition can optionally include one or more of a thickening agent, a pH adjusting agent, a tackifying agent, a tooth desensitizing agent, a flavoring agent, and a preservative.

The salt of boric acid can be included in the tooth whitening accelerator composition in an amount in a range of about 1 wt. % to about 50 wt. %, about 2 wt. % to about 40 wt. %, about 3 wt. % to about 30 wt. %, about 4 wt. % to about 20 wt. %, about 5 to about 10 wt. %, or about 6 wt. % to about 8 wt. % based on the total weight of the composition. Other suitable amounts of the salt of boric acid include, for example, about 1, 2, 3, 4, 5, 6, 7, 8, 9, 10, 15, 20, 25, 30, 35, 40, 45, or 50 wt. %. The salt of boric acid can be, for example, sodium borate, potassium borate, lithium borate, zinc borate, other salts of boric acid, and combinations thereof.

The polyol carrier can be included in the tooth whitening accelerator composition in an amount, for example, in a range of about 1 wt. % to about 90 wt. %, about 5 wt. % to about 80 wt. %, about 10 wt. % to about 70 wt. %, about 20 wt. % to about 60 wt. %, or about 30 wt. % to about 50 wt. %. Other suitable amounts of the polyol carrier include, for example, about 1, 2, 3, 4, 5, 6, 7, 8, 9, 10, 15, 20, 25, 30, 35, 40, 45, 50, 55, 60, 65, 70, 75, 80, 85, or 90 wt. %. In one embodiment, the amount of polyol carrier in the composition is greater than about 5 wt. %. The polyol carrier can be any polyol in which the salt of boric acid can be dissolved or dispersed. The polyol carrier can be, for example, a liquid. Alternatively, the polyol carrier can be a solid dissolved in a suitable solvent, such as water. For example, the polyol carrier can be triethylene glycol, propylene glycol, glycerin, polyvinyl alcohols, polyethylene glycol, polyvinyl alcohol copolymer, erythritol, arabitol, xylitol, ribitol, mannitol, sorbitol, dulcitol, iditol, isomalt, malitol, lacitol, polyglycitol, and combinations thereof.

The tooth whitening accelerator composition can further include a solvent. The solvent can aid in dissolving or dispersing, or diluting the salt of boric acid in the polyol carrier. Other functions of the solvent can be viscosity adjuster, co-solvent of other ingredients, and processing aid. The solvent can be included in the composition in an amount, for example, in a range of about 1 wt. % to about 90 wt. %, about 5 wt. % to about 80 wt. %, about 10 wt. % to about 70 wt. %, about 20 wt. % to about 60 wt. %, or about 30 wt. % to about 50 wt. %. Other suitable amounts of the solvent include, for example, about 1, 2, 3, 4, 5, 6, 7, 8, 9, 10, 15, 20, 25, 30, 35, 40, 45, 50, 55, 60, 65, 70, 75, 80, 85, or 90 wt. %. The solvent can be, for example, water. Other solvents include, but are not limited to, acetone, ethanol, isopropyl alcohol, methanol, butyl alcohol, hexane, and combinations thereof.

The tooth whitening accelerator composition can have a viscosity in a range of about 100 to about 10000 cps, measured at room temperature (about 20° C. to about 25° C.).

Other suitable ranges include, for example, about 200 cps to about 8000 cps, about 400 cps to about 6000 cps, about 600 cps to about 4000 cps, about 800 cps to about 2000 cps, about 1000 cps to about 10000 cps, about 3000 cps to about 9000 cps, about 7000 cps to about 8000 cps, about 5000 cps to about 7000 cps, about 100 cps to about 1000 cps, about 300 cps to about 900 cps, and about 500 cps to about 700 cps, as measured at 20° C. For example, the viscosity can be about 100, 200, 300, 400, 500, 600, 700, 800, 900, 1000, 2000, 3000, 4000, 5000, 6000, 7000, 8000, 9000, or 10000 cps, measured at room temperature. The viscosity can be adjusted to allow for a variety of application methods, including, for example, application by a brush, pad, ampoule, capsule, syringe, swab, sponge, pen, or other applicator. U.S. Pat. No. 7,201,577, the disclosure of which is incorporated herein by reference, describes an ampoule applicator suitable for use in applying the tooth whitening accelerator composition.

The viscosity of the accelerator composition can be adjusted, if needed, by adding a thickening agent. The thickening agent can be included in the tooth whitening accelerator composition, for example, in a range of about 0.1 wt. % to about 10 wt. %, about 0.5 to about 10 wt. %, about 1 wt. % to about 9 wt. %, about 2 wt. % to about 8 wt. %, about 3 wt. % to about 7 wt. %, about 4 wt. % to about 6 wt. %, or about 2 wt. % to about 6 wt. %. Other suitable thickening agent amounts include, for example, about 0.1, 0.2, 0.3, 0.4, 0.5, 0.6, 0.7, 0.8, 0.9, 1, 2, 3, 4, 5, 6, 7, 8, 9, or 10 wt. %. The thickening agent can be, for example, a polymer of an acrylic acid cross-linked with a polyalkenyl ether or a divinyl glycol, which is commercially available as CARBOPOL ETD 2020NF (Lubrizol, Ohio). Other thickening agents include, but are not limited to, celluloses, xanthan gum, alginates, fumed silica, polyvinylpyrrolidone and its copolymers, and combinations thereof.

Preferably, the tooth whitening accelerator composition has a pH of about 7 to about 12, about 7 to about 10, about 7 to about 9, about 8 to about 12, about 8 to about 10, or about 9 to about 12. For example, the tooth whitening accelerator composition can have a pH of about 7, 8, 9, 10, 11, or 12. The pH of the tooth whitening accelerator composition can further be adjusted using a pH adjusting agent in combination with the salt of boric acid. The pH adjusting agent can be included in the tooth whitening accelerator composition, for example, in a range of about 0.5 wt. % to about 25 wt. %, about 1 wt. % to about 20 wt. %, about 2 wt. % to about 18 wt. %, about 4 wt. % to about 16 wt. %, about 6 wt. % to about 14 wt. %, about 8 wt. % to about 12 wt. %, about 10 wt. % to about 25 wt. %, about 12 wt. % to about 22 wt. %, about 14 wt. % to about 20 wt. %, or about 16 wt. % to about 18 wt. %. Other suitable pH adjusting agent amounts include, for example, about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25 wt. %. The pH adjusting agent can be, for example, sodium hydroxide, potassium hydroxide, lithium hydroxide, calcium hydroxide, magnesium hydroxide, amine, sodium phosphate, potassium phosphate, and combinations thereof.

The tooth whitening accelerator composition can further include other additives such as a tooth desensitizing agent, a tackifying agent, a flavoring agent, and a preservative.

The tooth desensitizing agent can aid in lessening or preventing tooth sensitivity resulting from the whitening formulation. The tooth desensitizing agent can be included in the tooth whitening accelerator composition, for example, in an amount in a range of about 1 wt. % to about 20 wt. %, about 2 wt. % to about 15 wt. %, about 4 wt. % to about 10 wt. %, about 6 wt. % to about 8 wt. %, or about 4 wt. % to about 8 wt. %. Other suitable amounts of desensitizing agent include, for example, about 1, 2, 3, 4, 5, 6, 7, 8, 9, 10, 11, 12, 13, 14, 15, 16, 17, 18, 19, or 20 wt. %. The desensitizing agent can be for example, potassium nitrate, strontium chloride, sodium fluoride, ferric oxalate, and combinations thereof.

The tackifying agent can be included in the composition in an amount in a range of about 1 wt. % to about 20 wt. %, about 2 wt. % to about 18 wt. %, about 4 wt. % to about 16 wt. %, about 6 wt. % to about 14 wt. %, about 8 wt. % to about 12 wt. %, or about 1 wt. % to about 10 wt. %. Other suitable tackifying agent amounts include, for example, about 1, 2, 3, 4, 5, 6, 7, 8, 9, 10, 11, 12, 13, 14, 15, 16, 17, 18, 19, or 20 wt. %. The tackifying agent can be, for example, polyvinylpyrrolidone, starch, polyoxyalkylene, poly(methyl vinyl ether/maleic acid), polyvinyl alcohol, cellulose, xanthan gum, alginate and their copolymers, and combinations thereof.

The flavoring agent can be included in the composition, for example, in an amount in a range of about 0.01 wt. % to about 10 wt. %, about 0.05 wt. % to about 8 wt. %, about 0.1 wt. % to about 5 wt. %, about 0.5 wt. % to about 4 wt. %, about 1 wt. % to about 2 wt. %, about 1 wt. % to about 10 wt. %, about 2 wt. % to about 8 wt. %, or about 4 wt. % to about 6 wt. %. Other suitable flavoring agent amounts include, for example, about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 wt. %. The flavoring agent can be, for example, sucralose, acesulfame potassium, alitame, aspartame, anethole, cyclamate, glycyrrhizin, neotame, perillatine, saccharin, stevioside, inulin, natural or artificial essential oil, oleoresin, mint flavors, fruit flavors, and combinations thereof.

The preservative can be included in the composition, for example, in an amount in a range of about 0.01 wt. % to about 10 wt. %, about 0.05 wt. % to about 8 wt. %, about 0.1 wt. % to about 6 wt. %, about 0.5 wt. % to about 4 wt. %, about 1 wt. % to about 2 wt. %, about 1 wt. % to about 10 wt. %, about 2 wt. % to about 8 wt. %, or about 4 wt. % to about 6 wt. %. Other suitable preservative agent amounts include, for example, about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 wt. %. The preservative can be, for example, sodium benzoate, methyl paraben, propyl paraben, calcium propionate, disodium EDTA, BHT, BHA, and combinations thereof.

The tooth whitening accelerator composition can be made by mixing the salt of boric acid, the polyol carrier, and optionally a solvent to disperse or dissolve the salt of boric acid in the polyol carrier. For example, a solvent can be added when the polyol carrier is a solid. Mixing can be performed for a time in a range, for example, of about 30 second to about 30 minutes, about 1 minute to about 25 minutes, about 5 minutes, to about 20 minutes, or about 10 minutes to about 15 minutes. Other suitable mixing times can include, for example, about 30 seconds, 35 seconds, 40 seconds, 45 seconds, 50 seconds, 55 seconds, 1 minute, 5 minutes, 10 minutes, 15 minutes, 20 minutes, 25 minutes, or 30 minutes. A pH adjusting agent, solvent, and additives, such as desensitizing agents, flavoring, tackifying agents, and preservatives can be mixed together until homogenous and the mixture can optionally be added to the mixture of the salt of boric acid and the polyol carrier, and mixing can be continued until a homogenous mixture results, for example, for a time in a range, for example, of about 30 second to about 30 minutes, about 1 minute to about 25 minutes, about 5 minutes, to about 20 minutes, or about 10 minutes to about 15 minutes. Other suitable mixing times can include, for example, about 30 seconds, 35 seconds, 40 seconds, 45 seconds, 50 seconds, 55 seconds, 1 minute, 5 minutes, 10 minutes, 15 minutes, 20 minutes, 25 minutes, or 30 minutes. Optionally, a thickening agent can then be added to the mixture, and mixing can again be continued again until the mixture is homogenous, for example, for about 30 second to about 30 minutes, about 1 minute to about 25 minutes, about 5 minutes, to about 20 minutes, or about 10 minutes to about 15 minutes. Other suitable mixing times can include, for example, about 30 seconds, 35 seconds, 40 seconds, 45 seconds, 50 seconds, 55 seconds, 1 minute, 5 minutes, 10 minutes, 15 minutes, 20 minutes, 25 minutes, or 30 minutes. The thickening agent can be prepared by first mixing the thickening agent with a solvent, for example, water until the thickening agent is completely wetted by the solvent and a homogenous mixture is formed. Optionally, additional polyol carrier having additional preservatives dissolved therein can be added to the mixture, and mixing can be continued for a time in a range of about 10 minutes to about 120 minutes, about 20 minutes to about 100 minutes, or about 40 minutes to about 80 minutes. Other suitable mixing times can include, for example, about 10, 20, 30, 40, 50, 60, 70, 80, 90, 100, 110, or 120 minutes.

The tooth whitening accelerator composition can be used in a tooth whitening method by first applying the accelerator composition to at least one tooth. A tooth whitening formulation is then applied to the tooth, over the accelerator composition. Alternatively, the tooth whitening formulation can be applied to the tooth first and the accelerator composition can be applied over the tooth whitening formulation. In yet another, embodiment, the tooth whitening formulation and the accelerator composition can be mixed prior to application and then applied to the tooth in a single application step.

The tooth whitening formulation can include, for example, peroxide. Any known tooth whitening formulation containing a peroxide agent can be used in combination with the tooth whitening accelerator composition. Without intending to be bound by theory, it is believed that upon contact, the tooth whitening accelerator composition increases the pH of the tooth whitening formulation thereby enhancing and/or accelerating the activity of the tooth whitening formulation. For example, upon contact, the tooth whitening accelerator composition can increase the pH of the tooth whitening formulation to a pH in a range of about 5 to about 9. Most tooth whitening products are intentionally made at low pH level for the purpose of extension of shelf life. Peroxide, such as hydrogen peroxide and urea peroxide, is an oxidizing agent that can produce active free radicals, such as perhydroxyl radicals. These radicals react with the conjugated bonds within stain molecules, thereby causing conformational changes that disrupt stain structure. Without intending to be bound by theory, it is believe that at a low, acidic pH level, a greater amount less active radical species, such as $O^-$ radicals, are produced, as compared to more active radical species, such as $HOO^-$ radicals, that can be produced. The activity and concentration of the more potent free radicals are boosted in an alkaline environment. Upon contact with the accelerator composition of the disclosure, the pH of the tooth whitening formulation is increased from an acidic to a more basic level, which can improve the efficiency and enhance the whitening ability of the tooth whitening formulation.

The tooth whitening accelerator composition can be applied to at least one tooth using any known application method and/or applicator. The tooth whitening accelerator composition can be allowed to remain on the tooth prior to application of the tooth whitening formulation, for example, for a time in a range of about 1 second to about 60 seconds, about 2 second to about 50 seconds, about 4 seconds to about 40 seconds, about 6 seconds to about 30 seconds, about 8 seconds to about 20 seconds, or about 10 seconds to about 15 seconds. Other suitable times include, for example, about 1, 2, 3, 4, 5, 6, 7, 8, 9, 10, 15, 20, 25, 30, 35, 40, 45, 50, 55, or 60 seconds. For example, the tooth whitening accelerator composition can remain on the tooth for a time sufficient for the tooth whitening accelerator composition to dry before applying the tooth whitening formulation. Alternatively, the tooth whitening formulation can be applied immediately after application of the tooth whitening accelerator composition.

Additional aspects and details of the invention will be apparent from the following examples, which are intended to be illustrative rather than limiting.

EXAMPLES

Example 1

A tooth whitening accelerator composition was prepared by mixing glycerin and the sodium borate in a container for about 20 minutes. In a separate container, water, potassium phosphate, sucralose, sodium benzoate, and potassium nitrate were mixed until the mixture became homogenous. The mixture was then added to the sodium borate and glycerin mixture and mixing was continued until the resulting mixture became homogenous, about 30 minutes. A thickening agent was then added to the mixture and mixing was continued until the resulting mixture became homogenous. The thickening agent was first prepared by separately mixing the thickening agent in water until all of the thickening agent was wetted and became a homogenous mixture with the water. Methyl paraben and propyl paraben dissolved in propylene glycol was then added to the mixture and mixing was continued for about 60 minutes at 30 rpm, until a homogenous gel was formed. The ingredients of the composition were used in the amounts shown below.

| Ingredient | Function | Amount (% by weight of the total composition) |
| --- | --- | --- |
| DI Water | Solvent | 30.76 |
| Potassium Phosphate | pH adjusting agent | 5.00 |
| Glycerin | Polyol carrier | 10.00 |
| Potassium Nitrate | Tooth desensitizing agent | 5.00 |
| Sodium Borate | Salt of boric acid | 10.00 |
| DI Water | Solvent (for preparation of the thickening agent) | 32.72 |
| Carbopol ETD 2020NF | Thickening agent | 3.30 |
| Propylene Glycol | Polyol carrier | 3.00 |
| Sucralose | Flavor | 0.03 |
| Sodium Benzoate | Preservative | 0.05 |
| Methyl Paraben | Preservative | 0.11 |
| Propyl Paraben | Preservative | 0.03 |
| Total | | 100.00 |

The tooth whitening accelerator composition had a pH in a range of 7 to 9 and a viscosity in a range of about 7200 cps to about 8300 cps, measured at 25° C. using a Brookfield Viscometer DV-I Prime, with Spindle C at 10 rpm.

Example 2

A tooth whitening accelerator composition was prepared by the process of Example 1. The ingredients of the composition were used in the amounts shown below.

| Ingredients | Function | Amount (% by weight of the total composition) |
| --- | --- | --- |
| DI Water | Solvent | 34.76 |
| Potassium Phosphate | pH adjusting agent | 1.80 |
| Glycerin | Polyol carrier | 10.00 |
| Potassium Nitrate | Tooth desensitizing agent | 5.00 |
| Sodium Borate | Salt of boric acid | 9.20 |
| DI Water | Solvent (for preparation of the thickening agent) | 32.72 |
| Carbopol ETD 2020NF | Thickening agent | 3.30 |
| Propylene Glycol | Polyol carrier | 3.00 |
| Sucralose | Flavor | 0.03 |
| Sodium Benzoate | Preservative | 0.05 |
| Methyl Paraben | Preservative | 0.11 |
| propyl paraben | Preservative | 0.03 |
| Total | | 100.00 |

The tooth whitening accelerator composition had a pH in a range of 7 to 9 and a viscosity in a range of about 7200 cps to about 8300 cps, measured at 25° C. using a Brookfield Viscometer DV-I Prime, with Spindle C at 10 rpm.

Example 3

A tooth whitening accelerator composition was prepared by the process of Example 1. The ingredients of the composition were used in the amounts shown below.

| Element | Function | Amount (% by weight of the total composition) |
| --- | --- | --- |
| DI Water | Solvent | 32.72 |
| Potassium Phosphate | pH adjusting agent | 1.80 |
| Potassium Nitrate | Tooth desensitizing agent | 5.00 |
| Sodium Borate | Salt of boric acid | 10.00 |
| DI Water | Solvent (for preparation of the thickening agent) | 43.96 |
| Carbopol ETD 2020NF | Thickening agent | 3.30 |
| Propylene Glycol | Polyol carrier | 3.00 |
| Sucralose | Flavor | 0.03 |
| Sodium Benzoate | Preservative | 0.05 |
| Methyl Paraben | Preservative | 0.11 |
| Propyl paraben | Preservative | 0.03 |
| Total | | 100.00 |

The tooth whitening accelerator composition had a pH in a range of 7 to 9 and a viscosity in a range of about 7200 cps to about 8300 cps, measured at 25° C. using a Brookfield Viscometer DV-I Prime, with Spindle C at 10 rpm.

The invention has been described with reference to specific examples, which are intended to be illustrative only and not to be limiting of the invention. It will be apparent to those of ordinary skill in the art that changes, additions, and/or deletions may be made to the disclosed embodiments without departing from the spirit and scope of the invention.

What is claimed is:

1. A tooth whitening accelerator composition consisting of:
   a salt of boric acid (a) dissolved in a polyol carrier, or (b) dispersed in a polyol carrier, wherein, when the salt of boric acid is dispersed in the polyol carrier, the polyol carrier is included in the composition at a concentration greater than 5% by weight of the total composition; and optionally an additive selected from the group consisting of solvents, tooth desensitizing agents, tackifying agents, thickening agents, preservatives, flavoring agents, pH adjusting agents, and combinations thereof, wherein the preservatives are selected from the group consisting of sodium benzoate, methyl paraben, propyl paraben, calcium propionate, disodium EDTA, BHT, BHA, and combinations thereof,
   wherein the composition is orally acceptable.

2. The tooth whitening accelerator composition of claim 1, wherein the thickening agent is selected from the group consisting of a polymer of an acrylic acid cross-linked with a polyalkenyl ether or a divinyl glycol, celluloses, xanthan gum, alginates, fumed silica, polyvinylpyrrolidone and its copolymers, and combinations thereof.

3. The tooth whitening accelerator composition of claim 1, wherein the salt of boric acid comprises greater than 5 wt % of the total composition and up to about 50 wt % of the total composition.

4. The tooth whitening accelerator composition of claim 1, wherein the salt of boric acid is selected from the group consisting of sodium borate, potassium borate, lithium borate, zinc borate, other salts of boric acid, and combinations thereof.

5. The tooth whitening accelerator composition of claim 1, wherein the salt of boric acid comprises about 10 wt. % to about 50 wt. % of the total composition.

6. The tooth whitening accelerator composition of claim 1, wherein the polyol carrier is selected from the group consisting of triethylene glycol, propylene glycol, glycerin, polyethylene glycol, polyvinyl alcohol, erythritol, xylitol, ribitol, mannitol, sorbitol, isomalt, malitol, lacitol, polyglycitol, and combinations thereof.

7. The tooth whitening accelerator composition of claim 1, wherein the salt of boric acid is dissolved in the polyol carrier and the polyol carrier comprises about 1 wt. % to about 90 wt. % of the total composition.

8. The tooth whitening accelerator composition of claim 1, wherein the salt of boric acid is dispersed in the polyol carrier, and the polyol carrier comprises about 10 wt. % to about 70 wt. % of the total composition.

9. The tooth whitening accelerator composition of claim 1 wherein the tooth desensitizing agent is in an amount of about 1 wt. % to about 20 wt. % of the total composition.

10. The tooth whitening accelerator composition of claim 1 wherein the solvent is in an amount of about 1 wt. % to about 90 wt. % of the total composition.

11. The tooth whitening accelerator composition of claim 1 wherein the tackifying agent is in an amount of about 1 wt. % to about 20 wt. % of the total composition.

12. The tooth whitening accelerator composition of claim 1, wherein the thickening agent is in an amount of about 0.5 wt. % to about 10 wt. % of the total composition.

13. The tooth whitening accelerator composition of claim 1 wherein the preservative is in an amount of about 0.01 wt. % to about 10 wt. % of the total composition.

14. The tooth whitening accelerator claim 1 wherein the flavoring agent is in an amount of about 0.01 wt. % to about 10 wt. % of the total composition.

15. The tooth whitening accelerator composition of claim 1 wherein the pH adjusting agent is in an amount of about 0.5 wt. % to about 25 wt. % of the total composition.

16. The tooth whitening accelerator composition of claim 15, wherein the pH adjusting agent is selected from the group consisting of sodium hydroxide, potassium hydroxide, lithium hydroxide, calcium hydroxide, magnesium hydroxide, amine, sodium phosphate, potassium phosphate, and combinations thereof.

17. A method of whitening teeth, comprising:
applying one of the tooth whitening accelerator composition of claim 1 and a tooth whitening formulation to at least one tooth; and
applying the other one of the tooth whitening formulation and the tooth whitening accelerator composition to the tooth over the applied tooth whitening accelerator composition or tooth whitening formulation, after the application of the one of the tooth whitening accelerator composition and the tooth whitening formulation.

18. The method of claim 17, comprising applying the tooth whitening accelerator composition to the tooth and applying the tooth whitening formulation over the tooth whitening accelerator formulation.

19. The method of claim 17, comprising applying the tooth whitening formulation to the tooth and applying the tooth whitening accelerator composition over the tooth whitening formulation.

20. A method of making the tooth whitening accelerator composition of claim 1, comprising:
dissolving the salt of boric acid in the polyol carrier, or (b) dispersing the salt of boric acid in the polyol carrier to form a mixture; and
optionally thereafter adding an additive selected from the group consisting of solvents, tooth desensitizing agents, tackifying agents, thickening agents, preservatives, flavoring agents, pH adjusting agents, and combinations thereof.

21. The method of claim 20, comprising dissolving the salt of boric acid in the polyol carrier, wherein the polyol carrier comprises about 1 wt. % to about 90 wt. % of the total composition.

22. The method of claim 20, comprising dispersing the salt of boric acid in the polyol carrier, wherein the polyol carrier comprises about 10 wt. % to about 70 wt. % of the total composition.

23. A whitening product, comprising:
the tooth whitening accelerator composition of claim 1; and
a tooth whitening composition.

* * * * *

UNITED STATES PATENT AND TRADEMARK OFFICE
CERTIFICATE OF CORRECTION

PATENT NO. : 8,906,350 B2
APPLICATION NO. : 13/010526
DATED : December 9, 2014
INVENTOR(S) : Jianxun Feng It is certified that error appears in the above-identified patent and that said Letters Patent is hereby corrected as shown below:

In the Claims:

At Column 8, line 59, "accelerator claim" should be -- accelerator composition of claim --.

Signed and Sealed this
Seventeenth Day of November, 2015

Michelle K. Lee
*Director of the United States Patent and Trademark Office*